United States Patent [19]
Thode

[11] Patent Number: 5,892,072
[45] Date of Patent: Apr. 6, 1999

[54] C 12-16-90% FATTY ACIDS AND A PROCESS OF MAKING THE SAME

[75] Inventor: Kenneth C. Thode, Scituate, Mass.

[73] Assignee: Twin Rivers Technologies, LP, Quincy, Mass.

[21] Appl. No.: 787,370

[22] Filed: Jan. 22, 1997

Related U.S. Application Data

[63] Continuation-in-part of Ser. No. 588,981, Jan. 19, 1996, abandoned.

[51] Int. Cl.$^6$ ....................................................... C11B 3/12
[52] U.S. Cl. .............................................................. 554/175
[58] Field of Search ............................................. 554/175

Primary Examiner—Gary Geist
Assistant Examiner—Deborah D. Carr
Attorney, Agent, or Firm—Samuels, Gauthier & Stevens

[57] ABSTRACT

A continuous-steady state process of making a C 12–16–90% fatty acid from a whole cut fatty acid as well as the resulting product. The process includes fractionating a distilled or undistilled whole cut coconut fatty acid having 11–20% C 10 or less, 44–52% C 12, 13–19% C 14, 8–12% C 16, and 6–14% C 18 carbon chain links to form a top cut of C-12 and less any bottom cut of C 12–18. The C 12–18 is then fractionated to form a top cut of C 12–16–90% and a bottom cut of C 18. The top cut has a chain length distribution of about 2% maximum of C 10 or less, 56–66% C 12, 18–27% C 14, 9–17% C 16, and 3% maximum of C 18 carbon chain links.

14 Claims, 1 Drawing Sheet

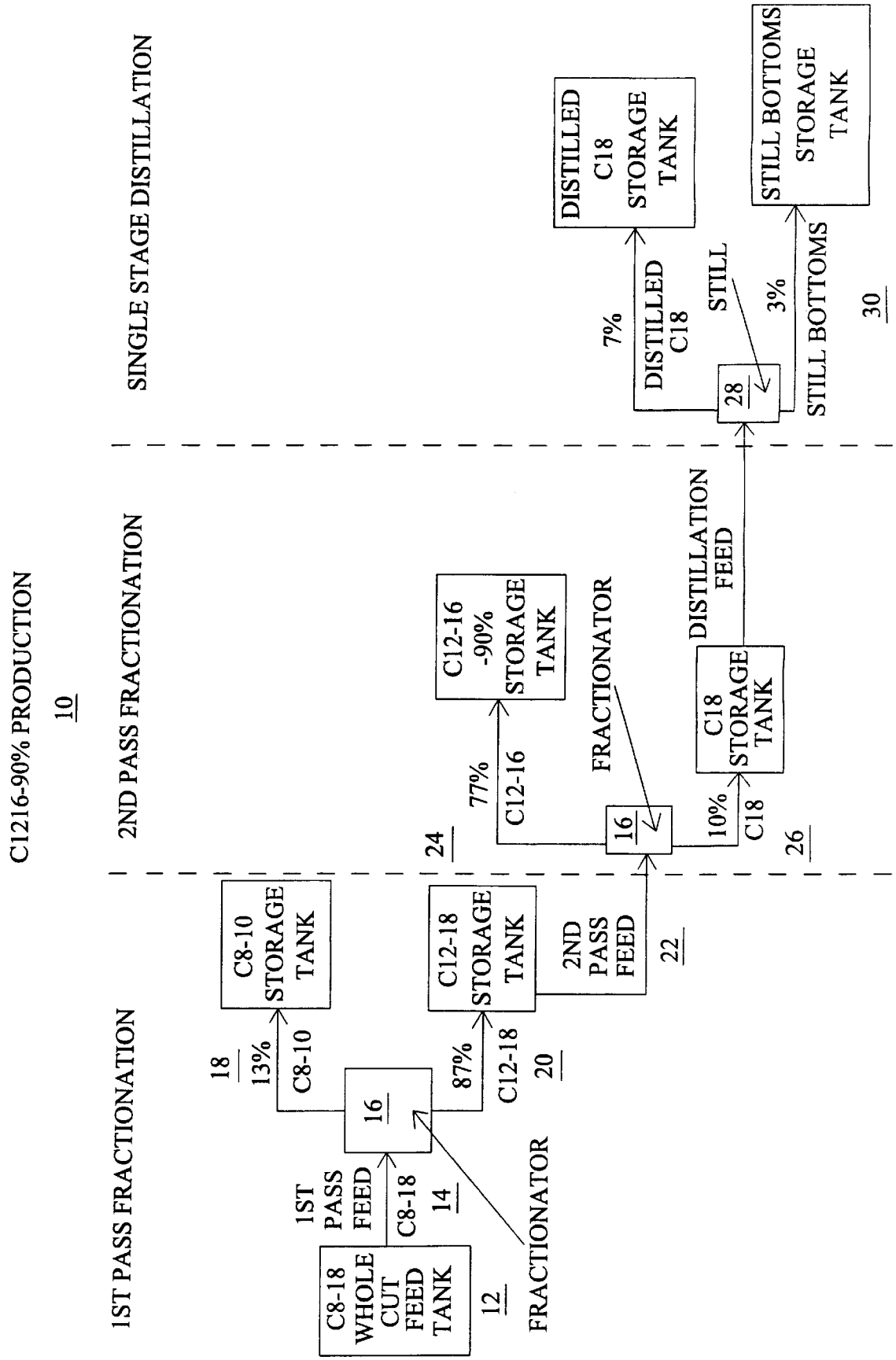

C 12-16-90% FATTY ACIDS AND A PROCESS OF MAKING THE SAME

This is a continuation-in-part of application(s) Ser. No. 08/588,981, filed Jan. 19, 1996, now abandoned.

BACKGROUND OF THE INVENTION

1. Field of the Invention

This invention is directed to a C 12–16 90% mid-cut fractionated fatty acid and a steady state manufacturing process to produce the same in commercial quantities. C 12–16–90% fatty acids may be substituted for Lauric, Myristic, C 12–14 or C 12–18 fatty acids in liquid soap products and detergents.

2. Description of the Prior Art

Fatty acids are made from naturally occurring fats and oils and comprise a mixture of different chain length hydrocarbons which are dependent on the natural distribution of the hydrocarbons in the oil feedstock. These fatty acids are referred to as whole-cut fatty acids. The resulting whole cut fatty acid is made by "splitting" the oil into fatty acid and glycerine in a hydrolyzer or kettle. The whole cut fatty acid will have the same distribution of carbon chain length molecules as the oil. As is commonly known and as exemplified in Bailey's Industrial Oil and Fat Products, Formo et at., Volume 1, Fourth Edition, pages 315 and 318, Lauric oils include the following approximate fatty acid chain length distributions:

|  | Coconut Oil | Palm Kernel Oil |
|---|---|---|
| C 10 and less | 11–20% | 6–12% |
| C 12 | 44–52% | 40–52% |
| C 14 | 13–19% | 14–18% |
| C 16 | 8–12% | 7–9% |
| C 18 | 6–14% | 13–26% |

See also the Fatty Acid Calculator ICD, Procter & Gamble, Industrial Chemicals Division, 1985; Nutritional Data sheet for "Typical Fatty Acid Profile for Neutresca 51–25" (Refined Coconut Oil), Aarhus Inc., Sept. 1994; Fatty Acid Specifications and (Typical) Properties sheet, Procter & Gamble Chemicals 10/93; and Product Specifications including Whole Distilled Coconut Fatty Acid (C8–C18), United Coconut Chemicals, Inc. Jan. 1996. As Coconut Fatty acids are derived from plants, the chain length distribution may vary depending on where the plants were grown, the environmental conditions, i.e. drought, temperature, etc.

Fatty acids may be purified by distillation. This results in a color and odor improvement of the fatty acid distillate and a dark still bottoms cut.

Fractionation or fractional distillation is practiced to separate the whole cut fatty acid, in either distilled or undistilled form, into particular chain lengths. This is accomplished by distilling over only the desired chain length(s) based on their different boiling points. This can be done to varying degrees of purity of separation up to 99%+. The resulting fractionated fatty acid will then contain only the specific chains desired for a product application. This can have improvements in odor, color, viscosity, product performance, etc.

There are different fatty acid products which may be produced from common coconut or palm kernel oil. Some examples follow. The examples are directed to a feedstock of coconut fatty acids, however, the processes would be very similar if the feed stock were changed to palm kernel oil. The general yields are specified for both feed stocks and are typical of those percentages of an undistilled whole cut coconut oil fatty acid.

There are many different types of fatty acid products in the marketplace including C 12–18 topped distilled, pure cut fractions and mid cut fractions. The C 12–18 topped distilled acid is a technical grade fatty acid cut whereby the fractions containing 10 carbon atoms and less have been largely removed. The C 12–18 contains the C 18 chain length which was included in the whole cut fatty acid. The yield of the C 12–18 topped distilled is about 77% having an Iodine Value ("I.V.") of 5–12. At an additional expense it can be hydrogenated down to a low (<l.5) I.V. for some product applications without impacting the yield.

As an alternative to the C 12–18 topped distilled cut, the C 12–18 fatty acid can be fractionated into pure cuts of specific chain lengths having a purity in the range of 90–99%. The pure cuts, however are expensive in comparison to the undistilled C 12–18 product due to the additional manufacturing steps required.

Optionally the C 12–18 bottoms cut can be fractionated into a mid cut C 12–14 product as a top cut and an undistilled C 16–18 bottoms cut. The C 12–14 mid cut fractionated fatty acid is a high quality color and odor acid with a typical I.V. of less than 0.5 and which may be used in liquid soap and detergent compositions.

During the transition from the manufacture of one product to the manufacture of another product, e.g., when switching or "lining out" from the production of C 12–99% to C 14–95%, a transitory C 12–16–90% product will be produced as a result of changing process conditions. However, the chain length distribution of this product will be skewed in that it will include only relatively small amounts of C 12's or C 16's, depending on the particular transition of products. For example, when transitioning from C 1299 to C 1416, a transitory C 12–16 product can be created with the following chain length distribution:

C 12:2.66% C 14:64.70% C 16:30.73% C 18:1.54%

Only small commercially insignificant amounts of such products are produced during the transition period.

A general objective of the present invention is to provide a fractionated C 12–16–90% fatty acid having naturally occurring levels of C 12's and C 16's to make the product useful in liquid soap and detergent compositions.

A companion objective is to provide a middle cut fraction where a whole cut fatty acid is stripped of the C 10 and lower chain lengths similar to C 12–18. Unlike C 12–18 it also has been additionally fractionated largely removing the C 18.

Another objective of the present invention is to provide a C 12–16–90% fatty acid as a lower cost substitute for more expensive Lauric, Myristic, C 12–14 or C 12–18 fatty acids in liquid soap products and detergents.

A further objective is to provide a continuous, steady state method of producing commercial quantities of a fractionated C 12–16–90% fatty acid which captures the vast majority of the C 12's and C 16's such that its yield will sufficiently qualify the product as a low cost substitute for C 12–14 in liquid soap and detergent compositions.

SUMMARY OF THE INVENTION

Broadly speaking, the present invention is directed to a continuous, steady state process of making a C 12–16–90% fatty acid from a whole cut fatty acid as well as to the resulting product. In a preferred embodiment to be hereinafter described in greater detail, the process includes fractionating a distilled or undistilled whole cut coconut fatty acid having 11–20% C 10 or less, 44–52% C 12, 13–19% C 14, 8–12% C 16, and 6–14% C 18 carbon chain lengths to form a top cut of C 10 and less and a bottom cut of C 12–18. The C 12–18 is then fractionated to form a top cut of C 12-16-90% and a bottom cut of C 18. The top cut has a chain length distribution of about 2% maximum of C 10 or less, 56–66% C 12, 18–27% C 14, 9–17% C 16, and 3% maximum of C 18 carbon chain lengths.

BRIEF DESCRIPTION OF THE DRAWING

The Figure is an illustrative process flow diagram.

DETAILED DESCRIPTION OF PREFERRED EMBODIMENT

Fractionation of whole cut fatty acids is conventionally accomplished by means of a distillation unit commonly referred to as a "fractionator". The feed stream is heated to a temperature which allows some vaporization to occur upon entry into the vessel. The residual liquid flows down through stripping stages consisting of structured packing to a still pot. The pot temperature is raised to the boiling point of the desired bottoms (longer chain length) product. A portion of the still pot liquid is vaporized. All of the vapor is condensed in the top section, with a portion of this liquid, the reflux, returning to the tower. This reflux is distributed over the upper sections of structured packing which act as rectifying stages. Longer chains are continuously condensed, purified and removed from the pot. Any impurities such as unsplit oil are removed with the bottoms. The shorter chains are continuously vaporized, purified and then condensed and removed in the top section of the tower. The entire process neither creates nor destroys the individual chain lengths present in the feed. The distillate and the bottoms material, if it contains multiple chain lengths, can be accumulated and reprocessed for further subdivision in a separate pass. The yield of specific cuts out of the process is directly proportional to the percentage in the whole cut fatty acid.

Referring to the Figure, a C 12-16-90% pure mid cut fractionated fatty acid distillate product having a high quality color and odor can be produced by fractionating an undistilled whole cut C 8-18 fatty acid of the above-described type as follows in a continuous, steady state process generally shown at 10:

1) A first pass 14 of a whole cut fatty acid 12 is first fractionated in a fractionator 16 forming a top cut 18 to remove a 13% content of C 8-10's and leaving an 87% undistilled C 12-18 bottoms cut 20. Those skilled in the art will recognize that during this processing phase, a small fraction of the C 8-10's (typically 2% maximum) will remain in the bottoms cut 20.

2) The 87% undistilled C 12-18 is fractionated in a second pass 22 to remove 77% C 12-16 as a top cut 24 leaving the 10% undistilled C 18 as a bottoms cut 26. The I.V. for the top cut 24 will have a maximum value of 3. Again, those skilled in the art will recognize that when the C 12-16's are separated from the C 18's, a small fraction of the C 18's (typically 3% maximum) will remain in the top cut 24.

3) The 10% C 18 is then single cut distilled at 28 to yield a 7% distilled C 18 product and a 3% still bottoms 30.

The yield of the C 12's, C 14's and C 16's in the C 12-16-90% is generally as follows:

| Carbon Chain Length | Percent |
|---|---|
| C 12 | 56–68 |
| C 14 | 17–27 |
| C 16 | 9–17 |

The C 10's or less and the C 18's will vary. They are dependent on the end use of the product and have maximum levels in order that the C 12–16 product remains not less than about 90% pure.

The total yield of the preferred product is generally as follows:

| Carbon Chain Lenqth | Percent |
|---|---|
| C 10 or less | 2 max |
| C 12 | 56–68 |
| C 14 | 17–27 |
| C 16 | 9–17 |
| C 18 | 3 max |

A more preferred product yield will include the following ranges:

| Carbon Chain Length | Percent |
|---|---|
| C 10 or less | 2 max |
| C 12 | 56–65 |
| C 14 | 19–23 |
| C 16 | 9–14 |
| C 18 | 3 max |

The total yield of the desirable C 8–10, C 12–16, C 18 distilled products produced from the whole cut fatty acid using the process of the present invention is greater than the final C 8–10, C 12–18 distilled products obtained when using the prior art methods of obtaining distilled C 12–18.

Substituting palm kernel oil as the feedstock in the above described continuous, steady state process, the yield of the C 12's, C 14's and C 16's in the C 12-16-90% is generally as follows:

| Carbon Chain Length | Percent |
|---|---|
| C 12 | 52–68 |
| C 14 | 18–24 |
| C 16 | 9–12 |

The C 10's or less and the C 18's will vary. They are dependent on the end use of the product and have maximum levels in order that the C 12–16 product remains not less than about 90% pure.

The total yield of the preferred product is generally as follows:

| Carbon Chain Length | Percent |
|---|---|
| C 10 or less | 2 max |
| C 12 | 52–68 |
| C 14 | 18–24 |
| C 16 | 9–12 |
| C 18 | 3 max |

A preferred product yield will include the following ranges:

| Carbon Chain Length | Percent |
| --- | --- |
| C 10 or less | 2 max |
| C 12 | 55–65 |
| C 14 | 19–23 |
| C 16 | 9–12 |
| C 18 | 3 max |

The specific process conditions for fractionating fatty acids are well known in the art and need not be described in detail.

EXAMPLE 1 C 12–16–90% vs. Pure Cuts

Whole cut fatty acid was fractionated into the pure cuts from C 8 to C 18. This required a fractionation pass for each chain length to be isolated. The total yield of desired pure cuts from a complete pure cut sequence was the same as the yield when processing C 8–10, C 12–16 and C 18 cuts in accordance with the present invention. The additional processing steps required for pure cuts makes them collectively more expensive. Where the purity of a specific chain length is required in a formulation, that investment is worthwhile. Where a broader chain length cut, such as C 12–16–90% can be substituted for pure cut(s), the added expense of pure cut manufacturing can be saved.

EXAMPLE 2 C 12–16–90% vs. C 12–14 –90%

From 100 lbs of whole cut fatty acid (C 8–18), 77 lbs of C 12–16 can be realized by the process of the present invention as compared to a yield of 68 lbs of C 12–14 with prior art methods. Each product requires an equivalent number of passes in the fractionator and thus incurs the same manufacturing expenses. When the C 12–16 is directly substituted for the C 12–14 in liquid laundry detergent for example, the fraction cut of C 10 and lower co-product is the same.

Additionally, during the production of C 12–16 there are 7 lbs. of pure cut C 18 realized as compared to 15 lbs. of C 16–18 produced during the production of C 12–14. The C 16–18 co-product has a lower economic value than the pure cut C 18. Consequently, after adding in the cost savings of the co-products, it is less expensive to produce the C 12–16.

EXAMPLE 3

C 12–16–90% vs. C 12–18 Distilled A comparison of the C 12–16–90% product of the present invention with a distilled C 12–18 product demonstrates similar yields. For example, both processes have a yield of 77 lbs of product from 100 lbs of whole cut fatty acid. The manufacturing of C 12–16–90% includes two passes through the fractionator. Whereas with the production of C 12–18 distilled, there is one pass through the fractionator, plus a single cut distillation step. The C 10 and lower co-products are the same. The 10 lbs. of undistilled C 18 produced from the C 12–16 are worth approximately three times the value of the 10 lbs of still bottoms from the C 12–18. The further processing step to distill C 18 only adds value. Consequently, the C 12–16–90% is a lower cost material than distilled C 12–18 after co-product credits.

EXAMPLE 4: Low IV C 12–16–90% vs. C 12–18 Distilled and Hardened

There is no change in the overall cost of producing a low I.V. C 12–16–90% fatty acid product as compared to a high I.V. C 12–16–90% product as the process parameters are simply adjusted to improve purity. However, to hydrogenate the distilled C 12–18, there is an additional processing step using steam, hydrogen, and catalyst. The expense is upwards of 10% of the overall material cost. Consequently the C 12–16–90% is a lower cost material to produce than the distilled and hydrogenated C 12–18.

The following table summarizes the discussion of Examples 1–4.

TABLE

COMPARISON OF FATTY ACID FRACTION YIELDS - Coconut Oil

| Chainlength Distribution Whole Cut Fatty Acid | | Topping One Pass To Remove Light Cut | Pure Cut Fractionation | | | | Mid Cut Fractionation | | | |
|---|---|---|---|---|---|---|---|---|---|---|
| | | | | | | | C 12-14 | | C 12-16 | |
| | | | Topping 1st Pass Light Cut | 2nd Pass Lauric Cut | 3rd Pass Myristic Cut | 4th Pass Palmitic Cut | 1st Pass Light Cut | 2nd Pass Mid Cut | 1st Pass Light Cut | 2nd Pass Mid Cut |
| C-10- | 13% | C-10-13% | C-10-13% | | | | C-10-13% | | C-10-13% | |
| C-12 | 50% | C 12-18 Undistilled 87% | C 12-18 Undistilled 87% | C-12 50% | | | C 12-18 Undistilled 87% | C 12-14 68% | C 12-18 Undistilled 87% | C 12-16 77% |
| C-14 | 18% | | | C 14-18 Undistilled 37% | C-14 18% | | | C 16-18 Undistilled 19% | | C-18 Undistilled 10% |
| C-16 | 9% | | | | C 16-18 Undistilled 19% | C-16 9% | | | | |
| C-18+ | 10% | | | | | C-18 Undistilled 10% | | | | |
| | 100% | 100% | 100% | 87% | 37% | 19% | 100% | 87% | 100% | 87% |
| FRACTIONATION BOTTOM CUT DISTILLATION | | Undistilled C 12-18 Distillation @88% Yld | | | | Undistilled C-18 Distillation @70% Yld | | Undistilled C 16-18 Distillation @80% Yld | | Undistilled C-18 Distillation @70% Yld |
| | | C-12 Distilled 77% | | | | C-18 Distilled 7% | | C 16-18 Distilled 15% | | C-18 Distilled 7% |
| | | Plus | | | | Plus | | Plus | | Plus |
| | | 10% Bottoms | | | | 3% Bottoms | | 4% Bottoms | | 3% Bottoms |

NOTE: ALL PERCENTAGES ARE OF THE WHOLE CUT UNDISTILLED FATTY ACID
NOTE: BOXED AREAS ARE FINISHED PRODUCTS FROM THE WHOLE CUT UNDISTILLED FATTY ACID

In summary therefore, it will be seen that the process of the present invention yields a C 12–16–90% product with a chain length distribution optimized to enable ready substitution for more expensive C 12–14, pure cuts or distilled C 12–18 products in liquid soap and detergent compositions. The product is produced continuously in commercial quantities under steady state conditions, and as such, stands in marked contrast to C 12–16 products produced during transitory processing conditions when lining out from one product to another. The percent purity of the fatty acid will depend on the end use of the fatty acid and will often be greater than 95% pure.

Having described the invention, what is now claimed is:

1. A continuous process for making a C 12–16–90% fatty acid from a whole cut fatty acid, said process comprising:
    a) fractionating a distilled or undistilled whole cut fatty acid typically having 6–20% C 10 or less, 40–52% C 12, 13–19% C 14, 7–12% C 16, and 6–26% C 18 carbon chain lengths to form a top cut of C 8–10 and a bottom cut of C 12–18;
    b) fractionating said C 12–18 to form a top cut of C 12–16–90% and a bottom cut of C 18; and
    c) recovering said C 12–16–90% top cut, said top cut having a typical chain length distribution of about 52–68% C 12, 17–27% C 14, and 9–17% C 16.

2. The process of claim 1, wherein the top cut has a 2% maximum of C 10 or less, and a 3% maximum of C 18 carbon chain lengths.

3. The process of claim 1, wherein the top cut preferably has a chain length distribution of about 2% maximum of C 10 or less, 55–65% C 1.2, 19–23% C 14, 9–14% C 16, and 3% maximum of C 18 carbon chain lengths.

4. The process of claim 1, wherein the C 12–16 is not less than about 90% pure.

5. The process of claim 1, wherein the C 12–16 is not less than about 95% pure.

6. The process of claim 4, wherein the C 12–16–90% pure has and I.V. of approximately 3 or less.

7. The process of claim 1, further comprising recovering said bottom cut of C 18.

8. The process of claim 7, further comprising distilling said bottom cut of C 18 to form a distilled, purified C 18.

9. The process of claim 8, further comprising recovering the distilled C 18.

10. The process of claim 1, wherein the process is run at or about steady state.

11. A substantially pure C 12–16 fatty acid comprising not less than 90% pure C 12–16, said C 12–16 fatty acid having 52–68% C12, 17–27% C14, and 9–17% C16.

12. The substantially pure C 12–16 fatty acid of claim 11, having about 2% maximum of C 10 or less, and 3% maximum of C18.

13. The substantially pure C 12–16 fatty acid of claim 11, preferably having about 2% maximum of C 10 or less, 55–65% C12, 19–23% C14, 9–14% C16 and 3% maximum of C18.

14. The substantially pure C 12–16 fatty acid of claim 11, having an I.V. of about less that 3.

* * * * *

UNITED STATES PATENT AND TRADEMARK OFFICE
CERTIFICATE OF CORRECTION

PATENT NO.    : 5,892,072
DATED         : April 6, 1999
INVENTOR(S)   : Kenneth C. Thode It is certified that error appears in the above-identified patent and that said Letters Patent is hereby corrected as shown below:

Title page,
Item [57], delete "C-12 and less any" and insert therefor -- C-10 and less and a --.

Signed and Sealed this

Sixteenth Day of July, 2002

Attest:

JAMES E. ROGAN
Attesting Officer    Director of the United States Patent and Trademark Office